United States Patent
Mathisen et al.

(10) Patent No.: US 10,105,401 B2
(45) Date of Patent: Oct. 23, 2018

(54) COMPOSITION COMPRISING BIOACTIVE AMINO ACIDS AND/OR PEPTIDES AND MARINE OIL IN A STABLE OIL-IN-WATER EMULSION, AND THE USE OF SAID COMPOSITION AS A FUNCTIONAL OR THERAPEUTIC COMPOSITION

(71) Applicant: SMARTFISH AS, Oslo (NO)

(72) Inventors: Janne Sande Mathisen, Oslo (NO); Henrik Mathisen, Oslo (NO)

(73) Assignee: Smartfish AS, Oslo (NO)

( * ) Notice: Subject to any disclaimer, the term of this patent is extended or adjusted under 35 U.S.C. 154(b) by 0 days.

(21) Appl. No.: 14/208,716

(22) Filed: Mar. 13, 2014

(65) Prior Publication Data

US 2014/0287054 A1  Sep. 25, 2014

Related U.S. Application Data

(62) Division of application No. 13/377,869, filed as application No. PCT/NO2010/000271 on Jul. 6, 2010.

(30) Foreign Application Priority Data

Jul. 6, 2009 (NO) .................................. 20092564

(51) Int. Cl.
| | | |
|---|---|---|
| *A61K 35/60* | (2006.01) | |
| *A23L 33/18* | (2016.01) | |
| *A23L 33/175* | (2016.01) | |
| *A61K 31/185* | (2006.01) | |
| *A61K 31/198* | (2006.01) | |
| *A61K 38/06* | (2006.01) | |
| *A23L 2/66* | (2006.01) | |
| *A23L 2/52* | (2006.01) | |
| *A61K 38/05* | (2006.01) | |
| *A61K 31/195* | (2006.01) | |
| *A61K 9/107* | (2006.01) | |
| *A61K 9/00* | (2006.01) | |

(52) U.S. Cl.
CPC ............... *A61K 35/60* (2013.01); *A23L 2/52* (2013.01); *A23L 2/66* (2013.01); *A23L 33/175* (2016.08); *A23L 33/18* (2016.08); *A61K 9/0095* (2013.01); *A61K 9/107* (2013.01); *A61K 31/185* (2013.01); *A61K 31/195* (2013.01); *A61K 31/198* (2013.01); *A61K 38/05* (2013.01); *A61K 38/063* (2013.01)

(58) Field of Classification Search
None
See application file for complete search history.

(56) References Cited

U.S. PATENT DOCUMENTS

| | | |
|---|---|---|
| 5,434,183 A | 7/1995 | Larsson-Backstrom |
| 5,514,670 A | 5/1996 | Friedman et al. |
| 6,440,464 B1 | 8/2002 | Hsia et al. |
| 6,451,341 B1 | 9/2002 | Slaga et al. |
| 6,620,440 B1 | 9/2003 | Hsia et al. |
| 7,041,324 B2 | 5/2006 | Myhre |
| 7,056,938 B1 | 6/2006 | Kammeijer et al. |
| 7,504,376 B2 | 3/2009 | Harris et al. |
| 8,017,170 B2 | 9/2011 | Decker et al. |
| 2004/0015000 A1 | 1/2004 | Aanesen et al. |
| 2004/0085058 A1 | 5/2004 | Mallet et al. |
| 2004/0087490 A1* | 5/2004 | Troup et al. ................. 514/2 |
| 2005/0209183 A1 | 9/2005 | Kippenberger et al. |
| 2009/0074933 A1 | 3/2009 | Mathisen et al. |
| 2009/0202679 A1 | 8/2009 | Mathisen |
| 2011/0027348 A1 | 2/2011 | Feher |

FOREIGN PATENT DOCUMENTS

| | | |
|---|---|---|
| JP | 2001078701 A | 3/2001 |
| NO | 322041 B1 | 8/2006 |
| NO | 323665 B1 | 6/2007 |
| NO | 324262 B1 | 9/2009 |
| SE | 518823 C2 | 11/2002 |
| WO | 8402271 A1 | 6/1984 |
| WO | 92/21335 A1 | 12/1992 |
| WO | 9221335 A1 | 12/1992 |
| WO | 95/05078 A1 | 2/1995 |
| WO | 9505078 A1 | 2/1995 |
| WO | 9847376 A1 | 10/1998 |
| WO | 0132034 A1 | 5/2001 |
| WO | 0147377 A2 | 7/2001 |
| WO | 2004112776 A2 | 12/2004 |

(Continued)

OTHER PUBLICATIONS

International Search Report and Written Opinion issued in International Application No. PCT/NO2010/000271, dated Oct. 7, 2010.
Norwegian Search Report issued in Norwegian Application No. 20092564, dated Jan. 21, 2010.
English translation of the Official Office Action issued in Norwegian Patent Application No. 20092564, dated Jan. 21, 2010 (3 pages).
English translation of the Official Office Action issued in Norwegian Patent Application No. 20092564, dated Sep. 18, 2012 (1 Page).
English translation of the Official Office Action issued in Norwegian Patent Application No. 20092564, dated Jul. 4, 2012 (2 pages).
English translation of the Official Office Action issued in Norwegian Patent Application No. 20092564, dated Jun. 18, 2012 (1 page).

(Continued)

*Primary Examiner* — Renee Claytor
*Assistant Examiner* — Srikanth Patury
(74) *Attorney, Agent, or Firm* — Fitzpatrick, Cella, Harper & Scinto

(57) ABSTRACT

The present invention relates to food supplements. Particularly, the present invention relates to a composition comprising marine oil in a stable oil-in-water emulsion, further comprising at least one specific bioactive amino acid or peptide, or derivatives thereof. In addition, the present invention relates to a process for the production of said composition and the use of said composition as a functional or therapeutic composition.

7 Claims, 3 Drawing Sheets

(56) References Cited

FOREIGN PATENT DOCUMENTS

| WO | 2007064222 A1 | 7/2007 |
|---|---|---|
| WO | 2009/027753 A1 | 3/2009 |
| WO | 2009027753 A1 | 5/2009 |

OTHER PUBLICATIONS

English translation of the Official Office Action issued in Norwegian Patent Application No. 20092564, dated Mar. 1, 2012 (2 pages).
English translation of the Official Office Action issued in Norwegian Patent Application No. 20092564, dated Sep. 21, 2011 (2 pages).
English translation of the Official Office Action issued in Norwegian Patent Application No. 20092564, dated May 9, 2011 (2 pages).
English translation of the Official Office Action issued in Norwegian Patent Application No. 20092564, dated Nov. 10, 2010 (2 pages).
English translation of the Official Office Action issued in Norwegian Patent Application No. 20120941, dated Jan. 4, 2013 (1 page).
Smartfish, "Nutrifriend 1100", Product Sheet, 2 pages.
Smartfish, "Recharge High Protein", Product Sheet, 1 page.
Denomega, "Pure Arctic 360 Premium", Master Product Information, 3 pages (Oct. 14, 2014).
Nutraceuticals, "L-Leucine", Product Specification, 2 pages (Jan. 8, 2014).
Moller's Dobbel Product Sheet, available at: http://www.mollers.no/produkt/mollers-dobbel-omega3/, 4 pages (May 13, 2016).
Glanbia Nutritionals (Ireland) Ltd., "PepForm® —Tryptophan Peptides", Product Data (Preliminary), Allergen Statement Non GM Statement, and Material Safety Data Sheet, Version 1, 5 pages (Aug. 2013).
Glanbia Nutritionals (Ireland) Ltd., "PepForm®—Arginine Peptides", Product Data (Preliminary), Allergen Statement, Non GM Statement, and Material Safety Data Sheet, Version 1, 5 pages (Aug. 2013).
European Search Report dated Jun. 27, 2018 in counterpart European Patent Application No. 18170573.2. (12 pages).
Database GNPD Mintel, Mar. 2004 (Mar. 2004), "Amino Calpis Eisaikei Milk", XP002782136, Database Accession No. 258286 (2 pages).

\* cited by examiner

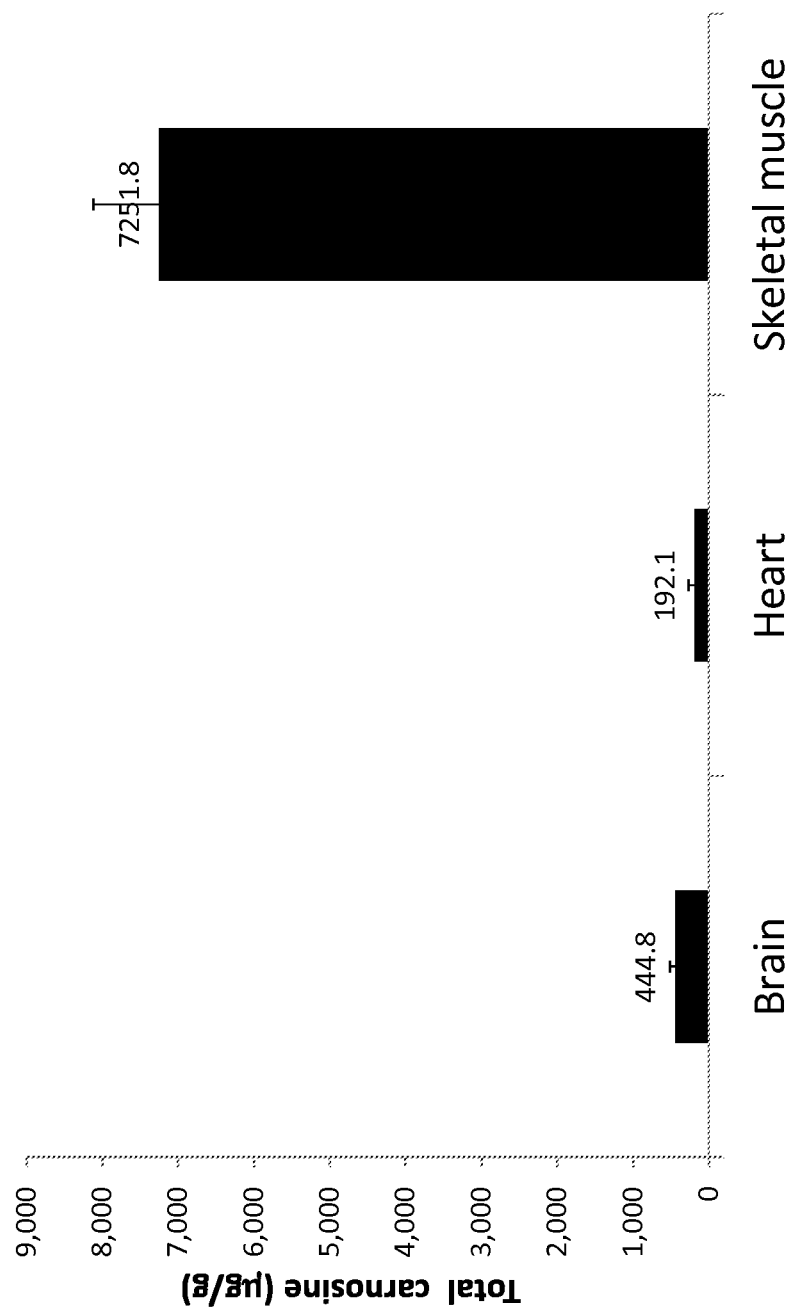

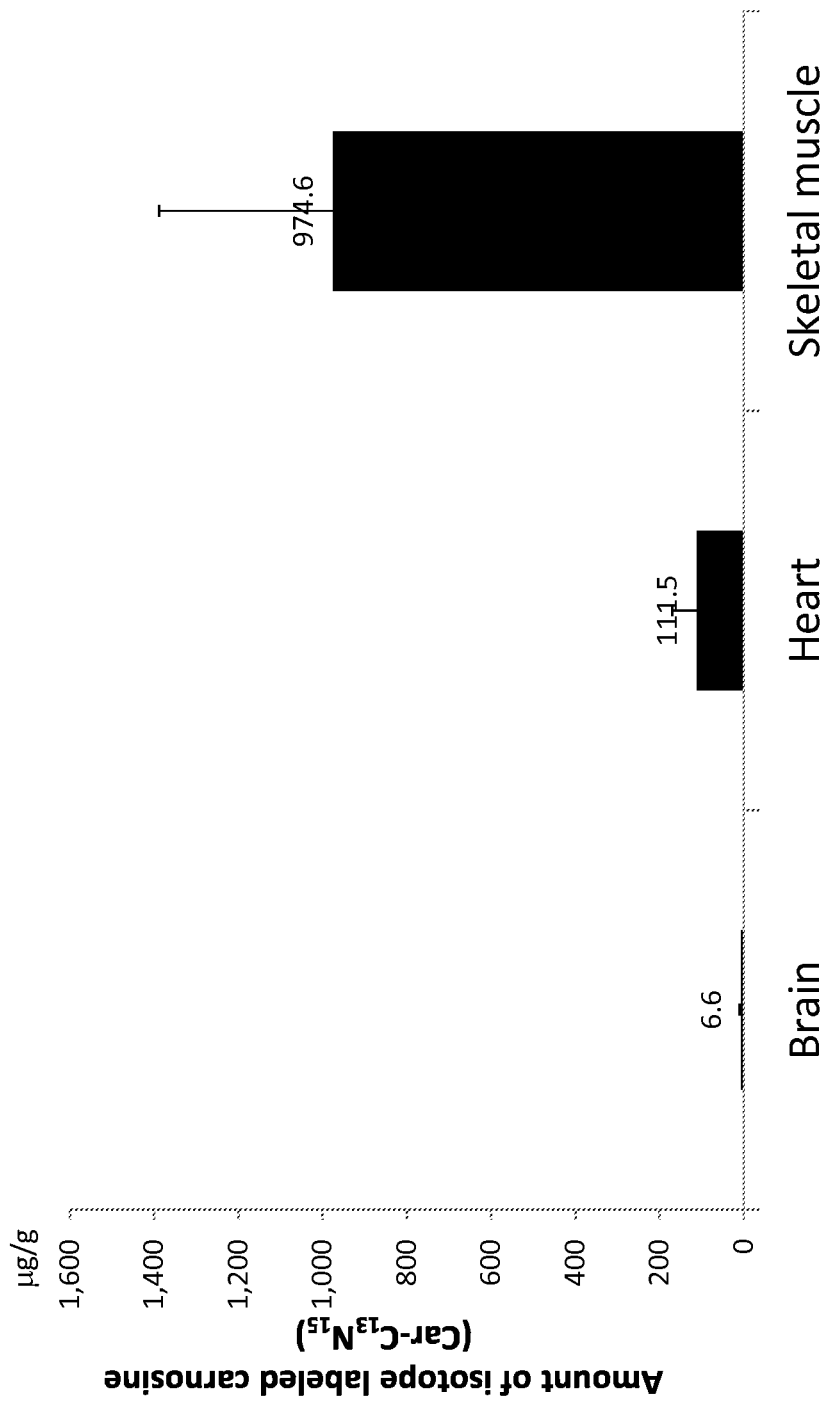

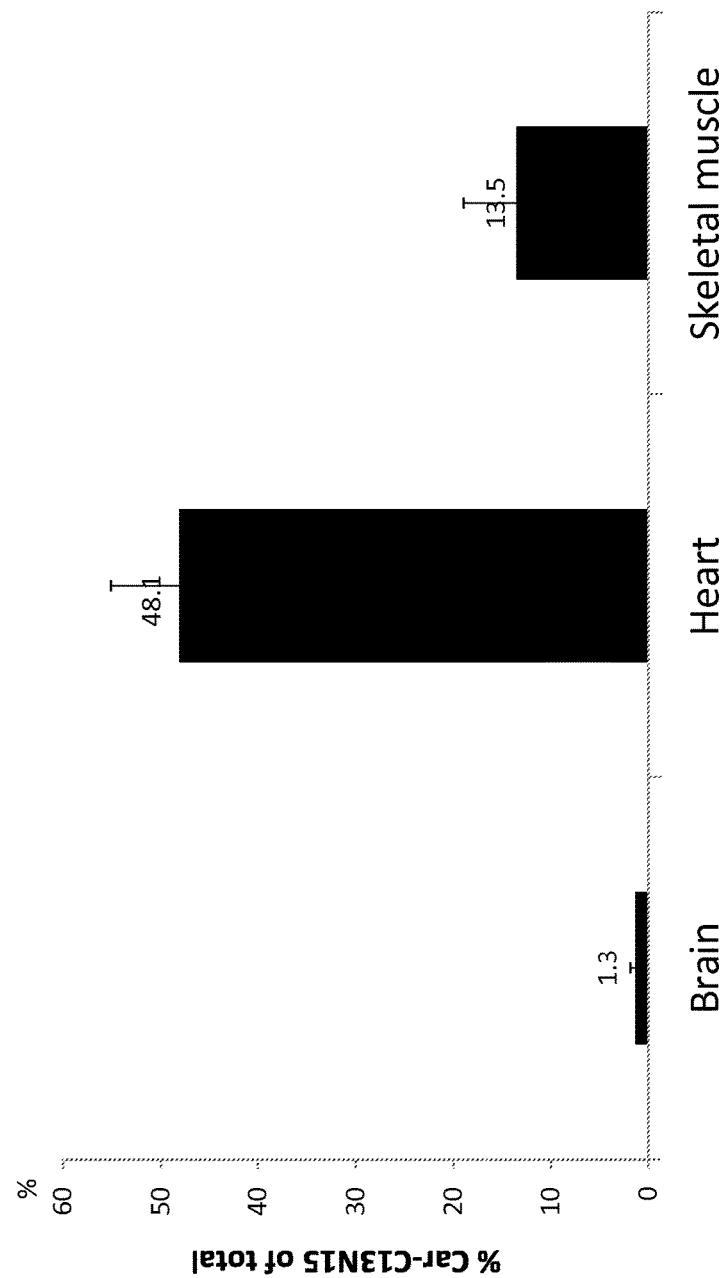

COMPOSITION COMPRISING BIOACTIVE AMINO ACIDS AND/OR PEPTIDES AND MARINE OIL IN A STABLE OIL-IN-WATER EMULSION, AND THE USE OF SAID COMPOSITION AS A FUNCTIONAL OR THERAPEUTIC COMPOSITION

CROSS-REFERENCE TO RELATED APPLICATIONS

This application is a divisional of U.S. patent application Ser. No. 13/377,869, filed Feb. 27, 2012, which is a 371 of International Application No. PCT/NO2010/000271, filed Jul. 6, 2010, which claims the benefit of Norwegian Application No. 20092564, filed Jul. 6, 2009, and incorporates by reference the entire disclosure of each of the mentioned U.S. prior and International applications.

FIELD OF INVENTION

The present invention relates to food supplements. Particularly, the present invention relates to a composition comprising marine oil in a stable oil-in-water emulsion, further comprising at least one bioactive amino acid or peptide, or derivatives thereof. In addition, the present invention relates to a process for the production of said composition and the use of said composition as a functional or therapeutic composition.

DESCRIPTION OF PRIOR ART

The health promoting effects of omega-3 fatty acids are well known. The health effects of various peptides and amino acids are partly known, but there is currently a strong scientific interest in their many biological functions.

Proteins are structural or functional. Biologically active proteins include enzymes, immunoglobulins, hormones, neurotransmitters, transport proteins, receptors etc. A balanced diet revealing adequate levels of biologically active peptides and amino acids are important. Imbalances may lead to disorders of the endocrine, neurological, cardiovascular, immune system, digestive system and metabolism, and also structural imbalances in the cell membranes and muscular system.

The building blocks of human proteins are twenty amino acids that may be consumed from both plant and animal sources. Of these 20 amino acids, 9 are considered to be essential; i.e. cannot be synthesized within the body. The remaining "nonessential" amino acids can be synthesized endogenously, so also the highly functional bioactive peptides.

Specific natural and synthetic peptides and amino acids have been shown to play a role in many disorders and diseases.

These include;
Neurological degeneration (Alzheimer's, Parkinson's, epilepsy depression, schizophrenia, mild cognitive impairment, dementia, stroke)
Autistic Spectrum Disorder, Asperger's, syndrome, ADHD, dyslexia, dyspraxia, Tourette's syndrome etc.
Cancer
Metabolic Indications
Diabetes
Blood pressure/Cardiovascular
Antimicrobial
Osteophorosis
Cardiovascular conditions
Oxidative stress conditions
Accumulations of damaged proteins
Positive impact on dopamine and serotonin production/balance Thus, it is a challenge to compose an adequate diet supplying the organism with sufficient amount of essential nutrients. To ensure adequate levels of specific bioactive peptides, and amino acids, these are also provided as food supplements.

However, there are reports indicating that oral administration is a challenge due to the fact that most peptides are unstable in the gastrointestinal (GI) tract and show low bioavailability. At present, it appears that nasal cavity is the preferred route for the delivery of peptides and protein drugs followed by vaginal, pulmonary, oral and transdermal routes, respectively.

A typical western diet contains a lot of proteins. The main sources of proteins in the diet are meat, chicken, milk and eggs. People with illnesses, who have been injured or are having severe stress, can benefit from a higher protein intake.

Recent scientific findings indicate that despite high intake of protein rich food, there might be a lack of amino acids, and importantly, the quality of the amino acids/peptides might be degenerated due to processing, unfavourable nutritional composition in the processed meats, long storage and harsh preparation before eating.

When frozen meat is thawed, juices and micro nutrients of the meat run out together with the ice water. It is likely that the antioxidant capacity of the amino acids and peptides in the meat will be reduced in frozen meat, because of the higher oxidation than in fresh meat.

An interesting French study ("*Determination of aromatic amino acid content in cooked meat by derivative spectrophotometry: Implications for nutritional quality of meat*" Ph. Gatellier, A. Kondjoyan, S. Portanguen, E. Grève, K. Yoon and V. Santé-Lhoutellier INRA, UR370 QuaPA, Centre de Theix, F-63122 Saint Genès Champanelle, France) showed that higher temperatures than 60 degrees have a dramatic effect on aromatic amino acids stability. The stability of the three aromatic amino acids during cooking decreased in the order tryptophan-phenylalanine-tyrosine.

An interesting Australian study (*Human requirements of essential amino acids and the composition of fresh and processed meats*. Dep. Animal Science, Queensland Agricultural College, Lawes, Australia) estimated protein, fat, ash and amino acids in fresh meat cuts, small goods and canned meat preparations. Essential amino acid (EAA) profiles were compared with the composition of model proteins constructed to meet established EAA requirements for children and adults. The EAA content of fresh meat proteins indicated high protein quality, but all meat preparations were of lower nutritional value.

Another interesting aspect is that cooking methods and doneness of meat are related to CRC (colorectal cancer) risk, higher temperature leading to higher risk. A 1991 Swedish case-control study showed that frequent consumption of fried meat with a heavily browned surface led to 3-fold increase in CRC risk. Since 1991, some twenty similar analytical studies have been published. Most studies confirm the Swedish findings: the intake of grilled, fried, barbecued and/or well-done red meat is more related to CRC risk than the intake of total red meat. This indicates that the health value of the meat and most likely the amino acids/peptides are reduced by harsh preparations.

Essential omega-3 fatty acids (DHA, EPA and DPA) have been investigated for a wide range of health conditions and diseases and found beneficial. These conditions are widely correlating with the ones found or indicated by various peptides.

The omega-3 polyunsaturated fatty acids (PUFA) are so important to the development and proper maintenance of the brain that some scientist even postulate that is was the ingestion of omega-3 that allowed the brain to evolve to the next stage in human development. While omega-3 was abundant in the human diet before the 20$^{th}$ century, omega-3 is now seriously lacking.

Not coincidentally n-3 fatty acids comprise approximately eight percent of the average human brain. Many scientists claim that DHA is structural and EPA is functional.

A benefit of omega-3 fatty acids is helping the brain to repair damage by promoting neuronal growth. Omega-3 fatty acids are instrumental in the function of brain cell membranes, which are important for the transmission of brain signals. By making cell membranes more fluid, omega-3 fatty acids, especially DHA, improve communication between the brain cells.

A number of studies have specifically examined the effect on an omega-3 deficient diet on dopamine and serotonin levels in animals. Not surprisingly, there are functional consequences when animals are fed on omega-3 deficient diets. Reduction in omega-3 intake results in a reduction of omega-3 content throughout the brain cells and organelles along with a compensatory rise in omega-6 fatty acids content. It is suggested in several studies that this alteration of the fatty acid composition in the membrane can alter neurotransmission and lead to a wide range of illnesses.

Following consumption, omega-3 can be incorporated into cell membranes and reduce the amount of arachidonic acid available for the synthesis of proinflammatory eicosanoids e.g. prostaglandins, leukotrienes. Likewise, omega-3 PUFA can also reduce the production of inflammatory cytokines.

Omega-3 fatty acids have been thoroughly examined for heart and cardiovascular health and found to be of great importance. Omega-3 has been shown beneficial for inflammation and oxidative stress conditions. Studies have also indicated positive effect on diabetes, osteophorosis, asthma, cancer etc.

The human body cannot synthesize omega-3 and the conversion from alfa-linolenic acid to long chain omega 3 is very limited—especially if there is a high intake of omega-6 from the diet. Intake of long chain omega-3 is needed from marine food sources, e.g. fish and seafood, or from supplements.

The omega-6 content in the typical protein food sources is very high and has risen dramatically during the last decades. The reason to this is primarily that animal feed has had an enormous increase in omega-6 fatty acids. It provides cheaper and more stable feed. The feed has a high content of plant oils and seed, even recycled cooking oils, leading to high levels of omega-6 in the animal and also in humans eating the omega-6 rich animals.

Laboratory tests of chickens have revealed lipid profiles of alarming omega 6: omega 3 ratio of up to 60:1. Many scientists believe the increase in chronic diseases is directly related to the change of dietary pattern, and changed nutritional value in foods over the 200 years. Our ancestors lived on a diet having an omega-6 to omega-3 ratio of 1:1, while our current dietary habits are closer to 10-20:1.

This means that proteins are mainly eaten together with high amounts of omega-6 fatty acids.

Knowing that omega-6 fatty acids are proinflammatory, and that processing and preparation of these protein rich foods often is high and harsh, it is highly questionable if the functions of the amino acids and peptides, including their antioxidant properties, are reduced or impaired.

Thus, there is a need for an oral formulation containing specific bioactive amino acids and/or peptides. Also there is a need for supplements containing omega-3 fatty acids. A combined formulation combining omega-3 fatty acids and specific bioactive peptides and/or amino acids resulting in increased absorption and bioavailability of the components of the composition is of great interest and will be highly appreciated in the market.

The present Applicant has previously invented a food supplement, i.e. a composition comprising omega-3 fatty acids in a stable oil-in water emulsion (Norwegian Patent No 322041). Different aspects of the composition are described in the applicants patents/patent applications. (Norwegian Patent No 322041 and 324262, and the Norwegian Patent Application NO 20073267).

It has now surprisingly been found that this stable oil-in-water emulsion is an excellent carrier for important biologically active peptides and/or amino acids.

The bioactive peptides and/or amino acids are thus formulated in a composition for oral administration, which has previously been a challenge due to the instability of the peptides in GI tract and low bioavailability.

The present invention provides a new composition combining the health promoting effect of bioactive amino acids and peptides together with the health promoting effect of omega-3 polyunsaturated fatty acids in a combined formula, revealing an oral formulation with improved bioavailability.

Without being bound to any theory, it is believed that the composition according to the invention protects the bioactive amino acids and peptides throughout the GI tract, and increases the bioavailability of the active ingredients. The omega-3 fatty acids of the composition will promote the penetration of amino acids and peptides through e.g. the blood-brain barrier and cell membranes, thus conferring the beneficial effects of both the polyunsaturated fatty acids and the bioactive peptides and amino acids.

PRESENT INVENTION

The present invention provides a new composition combining the health promoting effect of bioactive amino acids and peptides and the health promoting effect of omega-3 polyunsaturated fatty acids in a combined formula for oral administration.

High stability in the marine emulsion and composition enables low oxidation and keeps the vulnerable nutrients intact and potent, and makes it possible to provide tasty deliveries.

The ingredients of the composition are formulated and targeted toward specific conditions and diseases. For instance formulations for improving Alzheimer, autistic conditions, cancer conditions, diabetes, recovery and restitution, cardiovascular health, osteoporosis, asthma, depressions, muscle recovery and adaption to sports and endurance, are provided.

The composition reveals surprising characteristics as to bioavailability of the peptides and/or amino acids. Compared to prior art where corresponding amounts of omega-3 and peptides or amino acids are consumed in different, separate formulas e.g. pills, capsules, powders etc, the composition according to the present invention shows improved delivery, improved uptake and improved health impact.

Thus, one object of the present invention is to provide a composition combining specific potent and biologically active peptides and/or amino acids in an oral formulation.

Another object of the present invention is to provide a composition combining specific potent and biologically active peptides and/or amino acids and omega-3 fatty acids in an oral formulation.

Another object of the present invention is to provide a composition combining specific potent and biologically active peptides and/or amino acids and omega-3 fatty acids in an oral formulation, wherein said composition enhances the bioavailability of the active ingredients.

Yet another object of the present invention is to provide a composition combining specific potent and biologically active peptides and/or amino acids and omega-3 fatty acids in an oral formulation, in order to restore cell balance.

Yet another object of the present invention is to provide a composition combining specific potent and biologically active peptides and/or amino acids and omega-3 fatty acids in an oral formulation, in order to restore the neurological balance.

These and further aspects are achieved by the present invention.

Thus, one aspect of the present invention relates to a composition comprising at least one bioactive amino acid or peptide or derivative thereof and marine oil in a stable oil-in-water emulsion.

The bioactive peptides and/or amino acids of the invention include, but are not limited to, L-carnosine, or the precursors beta-alanine and histidine, glutahione or precursor cysteine or glutamine, food derived ACE inhibitory peptides, BCAA (branched chain amino acids) such as leucin, valin, isolecin, casein phospo peptides, collagen peptide, taurin and theanine. The content of the different bioactive peptides or amino acids may vary, but is preferably in an amount corresponding to the recommended daily dose.

The marine oil may be any oil rich in omega-3, e.g. fish oil, seal oil or krill oil. The oil may be mixed with other polyunsaturated oils of vegetable origin such as algae oil or herbal oil e.g. evening primrose oil and rapeseed oil.

One preferred embodiment of the present invention provides a composition wherein the content of the marine oil is about 0.5%-15% by weight. Within this range the following ranges are preferred: about 1.5%-7%, about 1.5%-5% and most preferably about 1.5%-3% or about 0.5%-7% and most preferably about 0.5%-3%. The marine oil may be selected from any marine oil preparation of appropriate quality. To be of appropriate quality the level of oxidation given as the totox-value (2 times the peroxide value (PV) added with the anisidine value (AV)) should be as low as possible and preferably below 10 and most preferably below 5. Said oils are clear oils with a very mild fishy odour and taste.

By a content of 5% the daily requirement of marine oil are reach by consuming about 50-100 ml of the composition according to the invention. The recommended daily dose of omega-3 for adults are 650 mg given by ISSFAL—International Society for the Study of Fatty Acids. The recommendation for children is about half the dosage of an adult, i.e. 350 mg.

For the preparation of the stable oil-in-water emulsion according to the invention any suitable emulsifier or combinations thereof, may be used. Milk solid, whey protein and pectin or any combination thereof are preferred emulsifiers.

The water phase of the oil-in water emulsion is preferably a water phase containing natural antioxidants e.g. fruit/vegetable juices, green tea, white tea and herbal tea. The water phase may also contain proteins such as soy, oat proteins, whey proteins and/or milk proteins.

The composition according to the invention may further comprise sweetener, flavouring agents, antioxidants, minerals, vitamins and preservatives. As such the composition may be given any desirable taste.

In another aspect of the present invention, the drink may be added prebiotics and/or probiotics. In another aspect of the present invention, the drink may be carbonated.

The composition may be in the form of any oral ingestible form. Thus, the consistency of the composition may vary from a liquid low viscosity drink to a more viscous drink, e.g. a smoothie. Further, the consistency of the composition may be creamy like yoghurt. Preferably, the composition according to the invention is a drinkable composition.

A further aspect of the present invention relates to a process for the production of the composition. In principle the composition is prepared as described in the previous patents/patent applications mentioned. Specific peptides or amino acids are added either in the water phase or directly to the emulsion after pasteurisation and/or homogenization.

One embodiment provides a process comprising the steps of:
a) bioactive amino acids and/or peptides and, if applicable, further water soluble additives are added to the water phase, together with a proportion of the emulsifier,
b) the rest of the emulsifier, and if applicable, oil soluble additives, are added to the oil phase,
c) the oil and water phase are mixed to a homogenous emulsion,
d) the emulsion obtained is optionally subjected to pasteurization and/or homogenization processes,
e) the obtained emulsion is cooled down and filled on clean disposable containers;
wherein all steps are performed under strict oxygen control.

Another embodiment provides a process comprising the steps of:
a) a proportion of the emulsifier and, if applicable, water soluble additives are added to the water phase,
b) the rest of the emulsifier, and if applicable, oil soluble additives, are added to the oil phase,
c) the oil and water phase are mixed to a homogenous emulsion,
d) the emulsion obtained is subjected to pasteurization and/or homogenization processes,
e) bioactive amino acids and/or peptides are added to the obtained emulsion,
f) the obtained emulsion is cooled down and filled on clean disposable containers;
wherein all steps are performed under strict oxygen control.

The clean disposable container is a preferably sealed container, made of any suitable material.

The composition in the form of a drink may be an functional drink, a medical drink or a drug delivery (in a drink format). Preferably, the drink has a base containing natural antioxidants e.g. fruit or vegetable juice, green tea, but any drinkable liquid may be used, including milk, soya milk, oat milk, rice milk.

A further aspect of the present invention relates a composition for use as a therapeutic drink. Further aspects relate to the use of a drink according to the invention for the production of a medical preparation for the prophylaxis or treatment of diseases associated with elevated oxidative stress, such as cancer, inflammatory disorders, neurological disorders, cardiovascular disorders and respiratory disorders.

The specific formulation of the invention is believed to be of great importance, presenting the essential nutrients and specific health promoting agents (omega 3 fatty acids and peptides and/or amino acids) to the digestive system and to the cells in a format highly beneficial to the cells and the body.

FIGURES

FIGS. 1A, 1B and 1C show the levels of carnosine and percent of newly synthesized carnosine in brain, heart and skeletal muscle. FIG. 1A) total carnosine; FIG. 1B) isotope labeled (C13, N15) carnosine and FIG. 1C) relative levels of isotope labeled carnosine of total carnosine in %. Error bars are standard error of mean. Mean values are specified on each bar.

EMBODIMENTS

The invention will now be further illustrated with reference to the following non-limiting examples.

Drink According to the Invention

Marine oil from Marine Harvest Ingredients or Denomega Nutritional Oil, were used in the preparation of all compositions. The totox value was below 5 and the preparation was conducted according to functional oil standards. The values are given as % by weight unless otherwise is stated.

EXAMPLE 1

Composition comprising fresh marine omega-3 emulsion, L-carnosine, selenium, zinc, iodine, and vitamin D.

|  | % |
|---|---|
| Water, purified | 81.00 |
| Pear Juice concentrate | 5.30 |
| Rosemary Extract 201 | 0.02 |
| Pomegranat juice conc | 2.40 |
| Aronina juice conc | 0.80 |
| Toco 50/vit E | 0.01 |
| Grindsted 3115 | 1.00 |
| Whey Protein Isolate (WPI) | 0.40 |
| Apple juice concentrate | 6.00 |
| Nat mandarine flavour | 0.15 |
| L-Carnosine | 0.4 |
| Selenium | 0.05 |
| Iodine | 120 mcg per unit |
| Vitamin D | 10 mcg per unit |
| Zinc gluconate | 0.005 |
| Fish oil | 3.0 |
| sum | 100.00 |

Suppliers:

Grindsted 3115, Toco 50 and Rosemary extract from Danisco

Nat mandarine flavour from Frey+Lau GmbH

L-Carnosine, Selenium, Iodine, Vitamin D and Zinc gluconate from K.W Pfannensmidt-Hamburg Fish oil from Denomega Nutritional Oils

EXAMPLE 2

Composition comprising fresh marine omega-3 emulsion, glutathione (reduced), selenium, B6 and B12

|  | % |
|---|---|
| Rosemary Extract 201 | 0.02 |
| Toco 50 | 0.01 |
| Grindsted pectin AMD 783 | 1.00 |
| Whey protein Isolate (WPI) | 0.40 |
| Apple concentrate | 6.05 |
| Pomegranate apple concentrate | 2.40 |
| Aronia concentrate | 0.80 |
| Pear concentrate | 6.49 |
| Water, purified | 80.00 |
| Orange/mandarine Flavour | 0.10 |
| Raspberry Flavour | 0.12 |
| Glutathione (reduced) | 20 mg per unit |
| Selenium | 50 mcg per unit |
| Vitamin B6 | 2 mg pr unit |
| Vitamin B12 | 1.00 mcg pr unit |
| Xalar salmon oil | 2.50 |
| Sum | 100.00 |

Suppliers:

Grindsted pectin AMD 783, Toco 50 and Rosemary extract from Danisco

Glutathione (reduced), L (+) selenium methionine, B6 and B12 from K.W Pfannensmidt-Hamburg Xalar salmon oil from Marine Harvest Ingredients

EXAMPLE 3

Comprising fresh marine omega-3 emulsion and theanine

|  | % |
|---|---|
| Rosemary extract 201 | 0.020 |
| Toco 50 | 0.010 |
| Grindsted 3115 | 1.00 |
| Whey protein | 0.45 |
| Apple concentrate | 6.23 |
| Pommegranat concentrate | 2.40 |
| Aronia concentrate | 0.88 |
| Pear concentrate | 5.56 |
| Water, purified | 81.40 |
| Orange/mandarine flavour | 0.10 |
| Raspberry flavour | 0.20 |
| Salmon oil, Xalar | 2.00 |
| Theanine | 0.10 |
| sum | 100.00 |

Suppliers:

Rosemary extract 201, Toco 50 and Grindsted 3115 from Danisco

Theanine from K.W. Pfannensmidt-Hamburg

Whey protein from Arta Foods

Natural flavouring agents from Firmenich

Salmon oil for Marine Harvest Ingredients

EXAMPLE 4

Composition comprising fresh omega-3 emulsion, taurine and zinc glutonate

|  | % |
|---|---|
| Rosemary extract 201 | 0.02 |
| Toco 50 | 0.01 |
| Grindsted 3115 | 1.00 |

-continued

|  | % |
|---|---|
| Apple concentrate | 3.23 |
| Pommegranat conc | 1.40 |
| White grape concentrate | 2.56 |
| Soya milk | 57.40 |
| Water, purified | 31.42 |
| Apricot flavour | 0.25 |
| Lemon flavour | 0.10 |
| Salmon oil | 1.50 |
| Taurine | 1.0 |
| Zinc gluconate | 12 mg per unit |
| sum | 100.00 |

Suppliers:

Rosemary extract 201, Toco 50 and Grindsted 3115 from Danisco

Natural flavouring agents from Firmenich

Taurine and zinc gluconate from K.W. Pfannenschmidt GmbH, Hamburg

Salmon oil for Marine Harvest Ingredients,

EXAMPLE 5

Process for Production

Water Phase

A tank is filled with purified and deionised water. The active ingredients in the form of peptides and/or amino acids or their derivatives or precursors are mixed in the water phase. Further, water soluble additives are added.

Oil Phase

The oil is mixed with rosemary extract, Toco 50 (an antioxidant preparation favourable to the stabilization of the oil). It is important that the oil is protected against oxidation during processing. Thereafter, the emulsifier or emulsifier combination is added, mixed gently at room temperature to a homogenous mixture. At least the oil soluble additives, e.g. flavouring agents are added.

Thereafter, the oil phase is added to the water phase.

Alternatively, the oil phase may be mixed with the water phase after which the emulsifier is added and an emulsion is obtained. The fruit concentrates are then added to the emulsion obtained and mixed thoroughly.

Alternatively, the emulsifier or emulsifier combination may be added partly to the water phase and partly to the oil phase.

The obtained emulsion may alternatively be subjected to a quick pasteurization (about 90° C. for 8 s), followed by homogenization and cooling to a temperature of 4-8° C.

As a further alternative, the active ingredients in the form of peptides and/or amino acids or their derivatives or precursors are added to the obtained emulsion after the pasteurization and homogenization step through specialized systems as Flexdose (Tetra Pack solution), or added into a sterile tank through an ultra pure process.

Finally, the drink is filled on airtight aseptic containers, preferably single dose containers, e.g. Tetra Brick about 200 ml and stored at 6-8° C. until use.

Strict oxygen control must be implemented in all steps to avoid oxidation of marine oil.

EXAMPLE 6

Carbonated composition comprising fresh omega-3 emulsion, beta-alanine and vitamine D3. Batch size 300 kg.

|  | % | kg |
|---|---|---|
| Rosemary extract 201 | 0.02 | 0.06 |
| Toco 50 | 0.01 | 0.03 |
| Pectin | 0.30 | 0.90 |
| Whey protein | 4.00 | 12.00 |
| Apple concentrate | 4.33 | 12.99 |
| Pomegranat concentrate | 2.40 | 7.20 |
| Aronia concentrate | 0.80 | 2.40 |
| Pear concentrate | 6.00 | 18.00 |
| Beta-alanine | 0.50 | 1.50 |
| Water, purified | 80.19 | 240.60 |
| Pomello flavour | 0.05 | 0.15 |
| Orange flavour | 0.16 | 0.48 |
| Trout oil | 1.20 | 3.60 |
| Soya lecitin | 0.01 | 0.03 |
| Vitamine D3 | 1.0 | 0.00001 |
| sum | 99.974 | 299.87 |

One Unit of 200 ml Contains:
Omega-3: 700 mg
DHA: 260mg
EPA: 260 mg
Beta-alanine: 1 g
Vitamin D3: 1.3 µg The composition were produced as follows:

Oil Phase

The oil is mixed with Rosemary Extract, Toco 50 (antioxidants). It is important that this is done immediately to protect the oil from oxidation. About 50% of the pectin is added and carefully stirred into the oil (at room temperature) until fully mixed. Then the aromas, i.e. pomello and orange is mixed into the oil. The rest of the pectin (50%) is blended into the deionized water in the tank. The whey protein powder has been blended/dissolved in the water several hours before.

Water Phase

Purified and deionized water is filled into a tank. Whey protein powder has been dissolved in the water for several hours. The oil phase is introduced in the water phase Emulsification The oil phase is mixed to the water phase and then emulsified. Mixing time approx. 4 min The fruit concentrates are blended into the emulsion and mixed thoroughly. Important that the least acid fruit concentrate is blended in first. Start with the pear concentrate and finish with the apple juice. Mixing time approx. 9 minutes. A rapid pasteurization—approx 90 degrees for 8 seconds.

Homogenisation

Temperature lowered to approx 75-78° C. Homoganisation at 75-78° C. and 75 Bar for approx. 30-35 seconds. Then temperature lowered to approx 4-8° C.

CO2 is added

Filling

Filled into aseptic Tetra Brick at 6-8 degrees.

EXAMPLE 7

The aim of this study was to investigate the uptake of β-alanine supplemented to "Smartfish" and its conversion to carnosine in skeletal muscle, heart and brain.

Smartfish denotes a commercially available drink from the company Smartfish containing 1000 mg omega-3 and 1.3 µg vitamin D3 per 200 ml.

Background and Summary of Results

β-alanine is a naturally occurring beta amino acid, which differs from L-β-alanine with respect to the amino group's position on the carboxylate group. Together with histidine, β-alanine makes up the dipeptide carnosine. Conjugation of β-alanine and histidine, catalyzed by carnosine synthetase, takes place inside the cell and β-alanine is the rate limiting precursor of carnosine. Carnosine concentrations in skeletal muscle can reach high levels (4-8 mmol/kg wet weight) and has been studied quite extensively in relation to effect on exercise and muscle recovery. Studies of athletes supplemented with β-alanine have demonstrated improvements in parameters of muscle function such as pH buffering and resistance to high intensity training. Animal studies have also revealed a carnosine dependent increase in sensitivity to $Ca^{2+}$, the latter also being noted in heart tissue. Studies in rodents have demonstrated a beneficial role of carnosine also in brain. Using a stroke model, carnosine elevation in brain protected against ensuing brain damage caused by occluding arteries to the brain. Thus, based on the aforementioned studies and others it has been suggested that supplementation of β-alanine can offer health benefits by raising the levels of carnosine.

In this study the aim was to investigate whether β-alanine as a constituent of Smartfish was taken up by skeletal muscle, heart and brain and incorporated into carnosine. We chose to label β-alanine with the two stable isotopes $C_{13}$ and $N_{15}$ in order to distinguish between carnosine made from endogenous β-alanine and carnosine made from supplemented β-alanine. Mice were orally administered with the β-alanine fortified Smartfish for one week and euthanized prior to sampling of the three tissues. The tissues were finally analyzed for the content of carnosine, both labeled and non-labeled.

We find that all the three tissues take up β-alanine during the one week feeding. In absolute values, the skeletal muscle had the highest levels of newly synthesized carnosine from the supplemented β-alanine, whereas brain had the lowest levels. In percent, the highest increase was found in heart. On average almost 50% of the total carnosine found in the heart was made up of supplemented β-alanine. The numbers in skeletal muscle and brain were 13.5% and 1.3% respectively.

Materials and Methods

Animal Experiments

β-alanine labeled with the stable isotopes $C_{13}$ and $N_{15}$ was purchased from Sigma-Aldrich and dissolved in Smartfish-juice (16.7 mg/ml). Five female mice (C57BL/6J) age 10 weeks were each supplemented with ~150 µl of the β-alanine fortified Smartfish two times each day for one week by oral gavage. This amount equals 200 mg/kg per day. After one week, the following organs were dissected out; gastrocnemius, heart and brain and immediately frozen in liquid nitrogen, and stored at −80° C.

Measurements of Carnosine in Tissues

Carnosine (Sigma-Aldrich) and 15N13C2-labeled carnosine (Sigma-Aldrich) concentrations in tissue were determined by HPLC-MS/MS operated in MRM mode.

Mouse tissues were homogenized in Methanolic HCL using a pellet grinder with cordless motor (Kontes). The homogenate was incubated for 30 min at 50° C. This procedure homogenized the tissue, precipitated proteins and methylated the carboxylic acid group.

After centrifugation, the supernatant were injected directly into the LC-MS/MS system. Calibrators were prepared by methylation of non labeled carnosine in methanolic HCl. The HPLC column used was a Zorbax XDB 150×4.6 mm ID with 5 µm particles. A gradient elution starting with 10% MeOH in water and 4 g/l ammonium acetate 40% MeOH for 3 minutes changing linearly to 100% methanol over 3.5 minutes was used to separate carnosine from other constituents.

Results and Discussion

Differential Uptake of β-alanine in Different Tissues

After one week of β-alanine+Smartfish supplementation, we assessed total and isotope labeled carnosine in brain, heart and skeletal muscle. As shown in FIG. 1A the total levels of carnosine was highest in skeletal muscle (7.250 g/g=32 mmol/kg), whereas the levels in brain and heart were 445 µg/g (1.97 mmol/kg) and 192 µg/g (0.85 mmol/kg) respectively. The levels of isotope labeled carnosine represent the β-alanine taken up through the diet. As shown in FIG. 1B, skeletal muscle has the largest absolute amounts of carnosine from the dietary β-alanine supplementation followed by heart and brain. Heart tissue has the highest relative levels of isotope labeled carnosine as to total carnosine with almost 50% of the total amount of carnosine consisting of $C_{13}N_{15}$ labeled carnosine. The corresponding values in skeletal muscle and brain are 13 and 1.3% respectively. Table 1 and 2 summarizes the data from all the individual samples in µg/g and mmol per kg wet weight, respectively.

In this study the main objective was to investigate whether β-alanine supplemented to Smartfish was taken up and conjugated with histidine to become part of carnosine in muscle, heart and brain. For that purpose, and because we used isotope labeled β-alanine, the present study included only a supplementation group. We have thus no information as of the relative increase in carnosine levels in the tissues compared with a control group. It is however pertinent to believe that almost all of the newly synthetized carnosine is adding to the net levels of carnosine in skeletal muscle during the one week feeding period. This assumption is based on a recent study showing that carnosine is relatively stable in muscle tissue (ref). In that study human volunteers were supplemented with β-alanine over a six week period, and levels of carnosine were then recorded in a "washout-"period of nine weeks. The results showed that levels of carnosine were only marginally reduced per week (2.5-3.5% reduction/week). Thus the newly synthesized carnosine reflects to a large extent a net addition in carnosine content. Accepting this, the increase in skeletal muscle carnosine is 17.8% after one week of supplementation, which is a significant and strong increase in such a short time period. Corresponding studies in mice do not exist, but in humans an average of 27% increase was found over a six week period, supplemented with 4.8 g β-alanine per day, which are amounts comparable to our supplementation.

For brain and heart, there are no comparable studies showing levels of carnosine as a function of β-alanine supplementation in a time dependent manner, thus our results calls for more studies particularly related to studies in heart. Of priority would be to investigate whether the labeled carnosine is manifested as a net increase. If that is the case it will be extremely interesting to investigate the physiological role of such an increase in heart tissue.

In summary the results show that β-alanine is bioavailable and taken up by all the three target tissues, when supplemented as part of Smartfish. The results also show that tissues respond differently in terms of uptake and incorporation into carnosine. The use of isotope labeled carnosine gave us more precise information about the relative uptake of β-alanine and some hints about the dynamics of the carnosine turnover. To our knowledge this approach for assessing carnosine levels has not been previously reported. However, the design of the study did not permit assessment of exactchanges in total carnosine levels as a result of β-alanine supplementation. The high proportion of newly synthetized carnosine in the heart is intriguing, and the results indicate that β-alanine is rapidly taken up and incorporated as a part of carnosine, and it would be very interesting to see whether this is manifested in a real increase concomitant with a physiological role. In brain, on the other hand, the low levels of newly synthesized carnosine indicate slower and less efficient uptake mechanisms of β-alanine. It is pertinent to speculate that a longer feeding period would increase the levels of labeled and hence newly synthesized carnosine in brain.

TABLE 1

Levels of carnosine (µg/g) in brain, heart and skeletal muscle following one week supplementation of Smartfish + $C_{13}N_{15}$ labeled β-alanine (200 mg/kg).

| Sample # | Natural carnosine | Carnosine labeled (Car-$C_{13}N_{15}$) | Total: Natural carnosine + Car-$C_{13}N_{15}$ | % Car-$C_{13}N_{15}$ of total | % Difference from natural to total carnosine |
|---|---|---|---|---|---|
| Brain 1 | 623.1 | 22.2 | 645.3 | 3.44 | 3.56 |
| Brain 2 | 543.1 | 3.0 | 546.1 | 0.55 | 0.55 |
| Brain 3 | 225.0 | 2.9 | 227.9 | 1.27 | 1.29 |
| Brain 4 | 403.3 | 2.6 | 405.9 | 0.64 | 0.64 |
| Brain 5 | 396.5 | 2.5 | 399 | 0.63 | 0.63 |
| Mean brain | 438.20 | 6.64 | 444.84 | 1.30 | 1.34 |
| Heart 1 | 145.5 | 338.7 | 484.2 | 69.95 | 232.78 |
| Heart 2 | 89.9 | 50.6 | 140.5 | 36.01 | 56.28 |
| Heart 3 | 73.5 | 100.9 | 174.4 | 57.86 | 137.28 |
| Heart 4 | 23.8 | 11.5 | 35.3 | 32.58 | 48.32 |
| Heart 5 | 70.4 | 55.9 | 126.3 | 44.26 | 79.40 |
| Mean heart | 80.62 | 111.52 | 192.14 | 48.1 | 111 |
| Skel. muscle 1 | 4 898 | 2 585 | 7 483 | 34.54 | 52.77 |
| Skel. muscle 2 | 9 201 | 549 | 9 751 | 5.63 | 5.97 |
| Skel. muscle 3 | 6 039 | 928 | 6 967 | 13.33 | 15.38 |
| Skel. muscle 4 | 7 249 | 443 | 7 693 | 5.77 | 6.12 |
| Skel. muscle 5 | 3 997 | 365 | 4 363 | 8.39 | 9.15 |
| Mean skel. muscle | 6277.3 | 974.6 | 7251.8 | 13.5 | 17.9 |

TABLE 2

Concentrations of carnosine in mmol per kg wet weight in brain, heart and skeletal muscle following one week supplementation of Smartfish + $C_{13}N_{15}$ labeled β-alanine (200 mg/kg).

| Sample # | Natural carnosine | Carnosine labeled (Car-$C_{13}N_{15}$) | Total: Natural carnosine + Car-$C_{13}N_{15}$ |
|---|---|---|---|
| Brain 1 | 2.76 | 0.098 | 2.855 |
| Brain 2 | 2.40 | 0.013 | 2.416 |
| Brain 3 | 1.00 | 0.013 | 1.008 |
| Brain 4 | 1.78 | 0.012 | 1.796 |
| Brain 5 | 1.75 | 0.011 | 1.765 |
| Mean brain | 1.94 | 0.03 | 1.97 |
| Heart 1 | 0.64 | 1.50 | 2.14 |
| Heart 2 | 0.40 | 0.22 | 0.62 |
| Heart 3 | 0.33 | 0.45 | 0.77 |
| Heart 4 | 0.11 | 0.05 | 0.16 |
| Heart 5 | 0.31 | 0.25 | 0.56 |
| Mean heart | 0.3567 | 0.4935 | 0.8502 |
| Skel. muscle 1 | 21.68 | 11.44 | 33.11 |
| Skel. muscle 2 | 40.72 | 2.43 | 43.15 |
| Skel. muscle 3 | 26.72 | 4.11 | 30.83 |
| Skel. muscle 4 | 32.08 | 1.96 | 34.04 |
| Skel. muscle 5 | 17.69 | 1.62 | 19.31 |
| Mean skel. muscle | 27.8 | 4.3 | 32.1 |

The invention claimed is:

1. A composition comprising an amino acid and marine oil selected from the group consisting of fish oil, seal oil and krill oil comprising omega-3 fatty acids in a homogeneous oil-in-water emulsion,
    wherein said amino acid is leucine,
    wherein the composition does not comprise an amino acid other than leucine,
    wherein an oil totox value is lower than 10,
    wherein the water phase of the oil-in-water emulsion comprises fruit juice, vegetable juice, green tea or herbal tea,
    wherein the homogeneous oil-in-water emulsion includes an emulsifier which is pectin, and
    wherein the content of marine oil is about 0.5-15% by weight.

2. The composition according to claim 1, wherein the content of marine oil is about 1.5-7% by weight.

3. The composition according to claim 2, wherein the content of marine oil is about 1.5-3% by weight.

4. The composition according to claim 1, further comprising sweeteners, flavouring agents, antioxidants and preservatives.

5. The composition according to claim 1, further comprising polyunsaturated vegetable oil.

6. The composition according to claim 1, wherein the composition is a drink.

7. A sealed container containing a composition as claimed in claim 1.

* * * * *